United States Patent [19]
Grieve et al.

[11] Patent Number: 5,492,695
[45] Date of Patent: Feb. 20, 1996

[54] **VACCINATING CATS AGAINST *DIROFILARIA IMMITIS* WITH AN L4 HOMOGENATE**

[75] Inventors: Robert B. Grieve, La Porte; Glenn Frank, Fort Collins, both of Colo.

[73] Assignee: Colorado State University Research Foundation, Fort Collins, Colo.

[21] Appl. No.: 882,790

[22] Filed: May 14, 1992

[51] Int. Cl.$^6$ .......................... A61K 39/00; A61K 35/56
[52] U.S. Cl. ........................................ 424/265.1; 424/520
[58] Field of Search .................................... 424/88, 265.1, 424/520; 435/69.3

[56] References Cited

U.S. PATENT DOCUMENTS

| | | | |
|---|---|---|---|
| 4,842,999 | 6/1989 | Fuller et al. | 435/7.22 |

FOREIGN PATENT DOCUMENTS

| | | |
|---|---|---|
| 0343480 | 5/1989 | European Pat. Off. . |
| WO92/13890 | 8/1992 | WIPO . |
| WO92/13560 | 8/1992 | WIPO . |
| WO93/10225 | 5/1993 | WIPO . |

OTHER PUBLICATIONS

Abraham et al. J. of Parasitol. 77(2):254–257 1991.
Abraham et al. Exp Parasitol 70(3) 314–22 1990 (see Abstract).
Weil. Exp. Parasitol 64:244–51 1987.
Culpepper, Jr. et al., "Molecular characterization of a *Dirofilaria immitis* cDNA encoding a highly immunoreactive antigen", *Molecular and Biochemical Parasitology*, vol. 54, No. 1, pp. 51–62, (1992) Amsterdam.
Hawkins, E. C., et al., *Kal Kan Forum* (1989) 8:2–7.
Philipp et al., "Biochemical and Immunologic Charcterization of a Major Surface Antigen of *Dirofilaria immitis* Infective Larvae", Journal of Immunology, 136(7):2621–27 (10986).
Denham, "Vaccination against Filarial Worms using Radiation–attenuated Vaccines", International Journal of Nuclear Medicine and Biology, 7:105–111 (1980).
Grieve et al., "Identification of *Dirofilaria immitis* Larval Antigens with Immunoprophylactic Potential Using Sera from Immune Dogs", The Journal of Immunology 148(8):2511–15 (1992).
Wang et al., "Parenteral Formulations of Proteins and Peptides: Stability and Stabilizers," Journal of Parenteral Science and Technology, 42(2S):S4–S9 (1988 Supplement).
Abraham et al., "Genetic Control of Murine Immune Responses to Larval *Dirofilaria immitis*", J. Parasitol., 76(4):523–28 (1990).
Young et al., "Efficient isolation of genes by using antibody probes", Proc. Natl. Acad. Sci. USA, 80:1194–98 (1983).
Noble et al., "Parasitology, The Biology of Animal Parasites", published by Lea & Febiger (Philadelphia), 9–20 (5th ed. 1982).

*Primary Examiner*—Mary E. Mosher
*Assistant Examiner*—Anthony C. Caputa
*Attorney, Agent, or Firm*—Sheridan Ross & McIntosh

[57] ABSTRACT

It has been found that hosts which are susceptible to nematode parasite infections can readily be protected from such infections when the parasites are not adapted for a parasite/host relationship to this host. In particular, feline hosts were immunized against heartworm using a variety of antigens derived from *Dirofilaria immitis* and related nematodes. Because cats are hosts susceptible to this nonadapted parasite, such antigens are successfully protective.

1 Claim, 4 Drawing Sheets

FIG. 1A

```
CGG AAT GAT CAT AAT TTA GAA AGC TAT TTT CAG ACG TAT CTG AGC TGG         48
Arg Asn Asp His Asn Leu Glu Ser Tyr Phe Gln Thr Tyr Leu Ser Trp
 1               5                  10                  15

CTC ACA GAT GCT CAA AAA GAT GAA ATT AAA AAA ATG AAA GAA GGA             95
Leu Thr Asp Ala Gln Lys Asp Glu Ile Lys Lys Met Lys Glu Gly
             20                  25                  30

AAA TCG AAA ATG GAT ATT CAA AAA AAA ATT TTT GAT TAT TTC GAA AGT        144
Lys Ser Lys Met Asp Ile Gln Lys Lys Ile Phe Asp Tyr Phe Glu Ser
 35                  40                  45

TTG ACA GGT GAT AAA AAG AAA AAG GCT GCA GAA GAA CTT CAA CAA GGT        192
Leu Thr Gly Asp Lys Lys Lys Lys Ala Ala Glu Glu Leu Gln Gln Gly
 50                  55                  60

TGC TTA ATG GCT CTC AGT GAA ATC ATT GGT AAT GAA AAG ATG CTT ATG        240
Cys Leu Met Ala Leu Ser Glu Ile Ile Gly Asn Glu Lys Met Leu Met
 65                  70                  75                  80

TTG AAA GAG ATT AAA GAT TCA GGC GCT GAT CCA GAA AAA GAA AGA ATG        288
Leu Lys Glu Ile Lys Asp Ser Gly Ala Asp Pro Glu Lys Glu Arg Met
             85                  90                  95

AAA GTC GAA GAT ATG TTG AAA CTT GTC GAC AAA GAA AAG AAG AAA            336
Lys Val Glu Asp Met Leu Lys Leu Val Asp Lys Glu Lys Lys Lys
            100                 105                 110

AGA ATT GAT GAA TAT GCT CCT GTA TGC CGT AAA ATT TAT GCG GCA ATG        384
Arg Ile Asp Glu Tyr Ala Pro Val Cys Arg Lys Ile Tyr Ala Ala Met
            115                 120                 125
```

FIG. 1B

```
AAT GAA CGG CGT AAG CGG AAT GAT CAT AAT TTA GAA AGC TAT TTT CAG      432
Asn Glu Arg Arg Lys Arg Asn Asp His Asn Leu Glu Ser Tyr Phe Gln
130                 135                 140

ACG TAT CTG AGC TGG CTC ACA GAT GCT CAA AAA GAT GAA ATT AAA AAA      480
Thr Tyr Leu Ser Trp Leu Thr Asp Ala Gln Lys Asp Glu Ile Lys Lys
145                 150                 155                 160

ATG AAA GAA GAA GGA AAA TCG AAA ATG GAT ATT CAA AAA AAA ATT TTT      528
Met Lys Glu Glu Gly Lys Ser Lys Met Asp Ile Gln Lys Lys Ile Phe
            165                 170                 175

GAT TAT TTC GAA AGT TTG ACA GGT GAT AAA AAG AAA AAG GCT GCA GAA      576
Asp Tyr Phe Glu Ser Leu Thr Gly Asp Lys Lys Lys Lys Ala Ala Glu
180                 185                 190

GAA CTT CAA GAA GGC TGC AGA GCT CTG AGA GAA AAA ATT GTT GGT GAA      624
Glu Leu Gln Glu Gly Cys Arg Ala Leu Arg Glu Lys Ile Val Gly Glu
        195                 200                 205

GAG AAG TGG ACT GTA TTG AGG CAA ATG AAG GAT TCA GGC GCA ACT CCA      672
Glu Lys Trp Thr Val Leu Arg Gln Met Lys Asp Ser Gly Ala Thr Pro
210                 215                 220

AAG GAA CTA AGC ATG AAA GTT GAA GAG ATG TTC AAA GAT GTC GTT GAC      720
Lys Glu Leu Ser Met Lys Val Glu Glu Met Phe Lys Asp Val Val Asp
225                 230                 235                 240

AAA GAT AAA AAG GAA AAA ATT GAT GAA TAT GCT CCT GTA TGC CGT AAA      768
Lys Asp Lys Lys Glu Lys Ile Asp Glu Tyr Ala Pro Val Cys Arg Lys
        245                 250                 255
```

FIG. 1C

```
ATC TTT GCG GTG ATA CAT GAA AGG CGT AAG CGG AAT GAT CAT AAT TTA    816
Ile Phe Ala Val Ile His Glu Arg Arg Lys Arg Asn Asp His Asn Leu
        260             265                 270

GAA AGC TAT TTT CAA ACG TAT CTG AGC TGG CTC ACA GAT GCT CAA AAA    864
Glu Ser Tyr Phe Gln Thr Tyr Leu Ser Trp Leu Thr Asp Ala Gln Lys
    275                 280                 285

GAT GAA ATT AAA ATG AAA ATG AAA GAA GGA GAA AAA TCG AAA ATG GAT ATT    912
Asp Glu Ile Lys Met Lys Met Lys Glu Gly Glu Lys Ser Lys Met Asp Ile
290                 295                 300

CAA AAA ATT TTT GAT TAT TTC GAA AGT TTG ACA GGT GAT AAA AAG    960
Gln Lys Ile Phe Asp Tyr Phe Glu Ser Leu Thr Gly Asp Lys Lys
305                 310                 315                 320

AAA AAG GCT GCA GAA GAA CTT CAA GAA GGC TGC AGA ATG GCT CTG AGA    1008
Lys Lys Ala Ala Glu Glu Leu Gln Glu Gly Cys Arg Met Ala Leu Arg
            325                 330                 335

GAA ATT GTT GGT GAA GAG AAG TGG ACT GTA TTG AGG CAA ATG AAG GAT    1056
Glu Ile Val Gly Glu Glu Lys Trp Thr Val Leu Arg Gln Met Lys Asp
        340                 345                 350

TCA GGC GCA ACT CCA AAG GAA CTA AGC ATG AAA GTT GAA GAG ATG TTC    1104
Ser Gly Ala Thr Pro Lys Glu Leu Ser Met Lys Val Glu Glu Met Phe
    355                 360                 365

AAA GAT GTC GTT GAC AAA GAT AAA AAG GAA AAA GAA ATT GAT GAA TAT GCT    1152
Lys Asp Val Val Asp Lys Asp Lys Lys Glu Lys Glu Ile Asp Glu Tyr Ala
370                 375                 380
```

FIG. 1D

```
CCT GTA TGC CGT AAA ATC TTT GCG GTG ATA CAT GAA AGG CGT AAG CGG     1200
Pro Val Cys Arg Lys Ile Phe Ala Val Ile His Glu Arg Arg Lys Arg
385                 390                 395                 400

AAT GAT CAT AAT TTA GAA AGC TAT TTT CAA ACG TAT CTG AGC TGG CTC     1248
Asn Asp His Asn Leu Glu Ser Tyr Phe Gln Thr Tyr Leu Ser Trp Leu
            405                 410                 415

ACG GAT GCT CAA AAA GAT GAA ATT AAA AAA AAA AAA                    1284
Thr Asp Ala Gln Lys Asp Glu Ile Lys Lys Lys Lys
    420                 425
```

5,492,695

VACCINATING CATS AGAINST *DIROFILARIA IMMITIS* WITH AN L4 HOMOGENATE

TECHNICAL FIELD

The invention is directed to methods to protect susceptible animals against infection by nematode parasites where the parasites are generally nonadapted to a long-term parasite/host relationship with the host. In particular, the invention concerns protection of cats against heartworm infection.

BACKGROUND ART

Parasitic infections generally depend on the ability of the parasite to establish a relationship with the host which, while detrimental to the robust good health of the host, is sufficiently benign to assure the parasite of a sufficiently long-term relationship to continue its own life cycle. An example of such a parasitic relationship is that of heartworm in dogs. Heartworm infection is very common and caused by the nematode, *Dirofilaria immitis*. Heartworm primarily affects dogs; indeed, in some geographical areas many canines are carriers of this parasite. On the other hand, only a relatively small number of cats in enzootic areas, probably less than 15%, harbor this nematode. It is currently not understood why cats, while susceptible, appear to react to infection differently from their canine counterparts.

Heartworm infection in dogs occurs through passage of the third stage larvae (L3) of *D. immitis* into the subcutaneous tissue as a result of a mosquito bite. In the subcutaneous tissue, the L3 larvae molt into a fourth larval stage (L4) which then migrates toward the thoracic cavity. A subsequent molt to an immature adult occurs and the immature adult gains access to the heart and pulmonary arteries where maturity into adulthood occurs. The L3 remain near the site of infection; L4 migrate through the cutaneous tissue and muscle and do not molt to the fifth stage until 50–70 days after infection. The adult *D. immitis* are on the order of 12–20 cm (males) and 25–31 cm (females) and produce motile vermiform embryos called microfilariae which are only 0.3 mm long. These embryos traverse capillary beds and circulate in the vascular system. There, the microfilariae are ingested by mosquitoes and continue their life cycle through L3 in the mosquito vector until infection of the host subsequent to the mosquito bite.

As heartworm infection is a recognized problem in dogs, various attempts have been made to prevent or treat this condition. While there have been a number of attempts to prepare vaccines against heartworm infection in dogs, it is clear that this is not a straightforward matter and that the success of a particular vaccine depends on the proper selection of the appropriate antigen. The nature of this antigen is not yet completely established. Because vaccines have not been practical, dogs have been treated with parasiticides after infection.

Cats do not ordinarily harbor heartworm parasites, and when they do, they are likely to die from the infection. It has not been possible to treat infected cats with parasiticides, because while treatment with parasiticides, in particular adulticides, is commonly practiced in dogs, it may be fatal in cats. In general, it is recommended that cats without overt signs of heartworm should not be treated (Hawkins, E. C. *Kal Kan Forum* (1989) 8:2–7). Cats exhibit severe post-adulticide reactions which often must be treated with oxygen supplementation and corticosteroid administration. Follow up treatment when microfilariae are present using a microfilaricide is also often necessary. Preventatives used in dogs have also been less successful in cats, are not currently approved for use in the United States and are generally not used.

In view of the substantial incidence of harmful heartworm infection in cats, and in view of the great risks associated with post-infection treatment, it would be highly desirable to produce a vaccine which would be protective against heartworm infection in felines, as well as other animals susceptible to but not adapted to a parasite/host relationship with heartworm. Cats, with respect to infection by *D. immitis*, are a model system of a susceptible host and a parasite which is not adapted to that host. As demonstrated herein, presumably because cats are not adapted to accommodate the heartworm parasite as are dogs, generic stimuli of the immune system are protective against infection. These stimuli include, for example, the administration of cytokines or of immunogens, e.g., proteins or other antigens associated with the various life stages of *D. immitis* and related nematodes, or mild viral infection.

DISCLOSURE OF THE INVENTION

The invention provides protocols and vaccines capable of protecting susceptible hosts against infection by nonadapted nematode parasites. In particular, cats are protected from infection by the nonadapted parasite *D. immitis*. Presumably because of the nonadaptation of the parasite, a spectrum of protocols to stimulate the immune system, such as immunization with antigenic substances derived from the parasite or substances related to these, is effective. In particular, for cats, antigens from *D. immitis* and related nematodes may be used as the active components of a vaccine.

Thus, in one aspect, the invention is directed to a method to protect susceptible hosts against infection by nonadapted nematode parasites, which method comprises stimulating the immune system of the host by administration of immunostimulants, such as cytokines, or by administering to the host a protective amount of an antigen derived from the nonadapted nematode parasite or other nematode. In the case of cats, *Dirofilaria immitis* represents a suitable nonadapted parasite. In other aspects, the invention is directed to pharmaceutical or vaccine compositions useful in the invention method.

BRIEF DESCRIPTION OF THE DRAWINGS

FIG. 1 SEQ ID NO: 3 and SEQ ID NO; 4 shows the DNA encoding the immunogenic protein Di22 and the deduced amino acid sequence of this protein.

MODES OF CARRYING OUT THE INVENTION

The invention is based on the discovery that hosts which are susceptible to infection by a nematode parasite, but for which host an effective parasite/host relationship has not been developed, can be protected altogether from infection by these nonadapted parasites by the use of generalized immune stimulants such as a wide spectrum of antigens derived from this parasite or other nematodes. Thus, for example, while prevention of heartworm infection in dogs requires specific antigens capable of providing the most effective immune responses, hosts which are not ordinarily infected by heartworm, such as cats, can easily be protected by immunization with undefined extracts of the nonadapted nematode. The inventors herein have thus established that immunization by antigens in general derived from parasites not adapted for infection of a particular host, but wherein the host is susceptible to infection by the parasite, are effective in preventing infection in these hosts.

Thus, as used herein, the terms "susceptible" host and "nonadapted" parasites are used in conjunction with each other. The susceptible host is capable of being infected by the parasite, but the parasite is not adapted to the susceptible host in such a way that a long-term parasite/host relationship can be established as in the case of "normal" hosts. Thus, the susceptible hosts are infrequently infected, but when infection occurs, it is serious and often fatal.

The method of the invention is grounded in the discovery that because the feline host is not adapted to support the growth of the heartworm parasite, a wider range of immunogens can be used to confer immunity than would be possible for hosts adapted to the growth of the parasite. Thus, in a generalization of this finding, susceptible hosts may be protected from infection by nematode parasites by any protocol that operates as a general immune system stimulant. In one approach, the immune system can be stimulated to operate at an elevated level at the time of challenge by the parasite by administering to the host generic immunostimulants such as cytokines or other medicaments known to elevate the response of the immune system generally. Such immunostimulants include, for example, interleukins such as IL-2 and colony-stimulating factors such as GCSF and GMCSF. Methods for elevating immune system performance are known generally, and such protocols may be used to advantage in the present invention.

In the alternative, or in addition, the susceptible host may be immunized using antigens derived from nematodes in general, including both parasitic and free-living forms. It appears to be unnecessary that the nematode be related to the nematode parasite against which protection is desired; however, in a preferred embodiment, the parasites to which the hosts are susceptible but to which they are not adapted, or nematodes related to these parasites, are preferred. (It should be noted that although "nonadapted" as an adjective is generally applied to the parasite, it is actually a mutual adaptation that is being described. Thus, "nonadapted" parasite includes adaptations which are made in the metabolism of the host, as well as in the metabolism of the parasite.) By "derived from" a nematode is meant that the counterpart of the antigen exists in the nematode, and does not necessarily imply that the antigen as used is, in fact, physically extracted from the nematode in question. For purposes of illustration, cats are used herein as the susceptible host, and heartworm infection caused by *D. immitis* is the corresponding nonadapted parasite.

The antigens useful in the method of the invention using cats as hosts are derived from *Dirofilaria immitis* or related nematodes. They can be isolated from parasite culture, necropsy specimen or can be synthetically or recombinantly produced. By "derived from" is meant that the antigen in question exists in *D. immitis* or a related nematode. Its actual production need not be by isolation therefrom.

It has been found that, in addition to vaccine components identifiable in larval stages of *D. immitis* which are effective in dogs, it is also possible to substitute larval immunogens which are not effective in dogs or immunogens that may be isolated from additional life cycle stages of this nematode, including the adult form, as well as the various life stages of related nematodes.

U.S. patent application Ser. No. 07/683,202, filed 8 Apr. 1991 and incorporated herein by reference, describes a particular protein, designated therein "Di22". Proteins such as Di22 can be used in cats. In addition, as set forth below, U.S. Ser. No. 07/792,209, filed 12 Nov. 1991, describes proteases isolatable from the L3 and L4 larval stages of the *D. immitis* parasite. These vaccine components are useful in both dogs and cats. On the other hand, the active immunogen in vaccines effective against cats may be derived from L1, L2, L5 or adult of *D. immitis* or may be derived from related nematodes—specifically, those nematodes which are capable of infecting mammalian hosts. Such nematodes include *Onchocerca cervipedis, O. cervicalis, Brugia malayi*, Trichostrongylus, Haemonchus, Ostertagia, Nematodirus, *Parascaris equorum, Ascaris suum, Toxascaris leonina, Toxocara canis, Toxocara cati*, Ancylostoma, Uncinaria, Strongyloides, or any other nematode capable of sustaining a parasitic relationship with a host or a free-living nematode such as *Caenorhabditis elegans*. In general, the active vaccine component(s) may be derived from related nematodes such as those set forth above, or any nematode capable of sustaining a parasitic relationship with a host, or even free-living nematodes.

For isolation of an antigen or DNA encoding it, the nematodes can be cultured in vitro under suitable conditions to provide various larval stages as described by Abraham, D. et al. *J Parasitol* (1987) 73:377–383. Briefly, for *D. immitis*, the mosquito *Aedes aegypti* Liverpool (black eyed strain) are infected with *D. immitis* by feeding on microfilaremic blood obtained from experimentally infected animals. 15 days after feeding, the mosquitoes are anaesthetized, surface sterilized, and placed on screens in funnels filled with a 1:1 mixture of NCTC-135 and Iscove's modified Dulbecco medium (Sigma) containing 2.5 µg/ml amphotericin B; 100 µg/ml gentamycin; 50 µg/ml sulfadiazine; and 10 µg/ml trimethoprim. The larvae are collected from funnels 90 minutes post-incubation. The cultures are maintained at 10 L3 organisms per ml of medium at 5% $CO_2$ and saturated humidity. The L3 larvae are cultured at 37° C. in the foregoing medium, supplemented with 20% fetal calf serum for 1–8 days.

Alternatively, 10 days after feeding, the mosquitoes are anesthetized and the worms are recovered by dissecting the heads and allowing the worms to emerge into medium with 20% Seru-max (Sigma) to induce molting. After 48 hours, the worms are recovered, washed 5 times in medium which does not contain Seru-max, and recultured. The L3 larval stage is maintained for about 96 hours in culture on Seru-max-free medium; molting to L4 then occurs and L4 is maintained up to 144 hours. These L3 and L4 larval stages are particularly useful as sources for antigens to provide the active ingredients for the invention vaccines.

For example, protease components of the L3 and L4 larval stages are described in copending application U.S. Ser. No. 07/792,209, filed 12 Nov. 1991 and incorporated herein by reference. General methods to identify antigenic components are also described in copending application Ser. No. 07/654,226, filed 12 Feb. 1991 and incorporated herein by reference. In addition to direct isolation of native antigens from the various larval stages of *D. immitis* or a related nematode, the antigens can be recovered using cDNA libraries prepared therefrom and produced recombinantly. Particularly useful components of the larvae can be identified by preparing the cDNA as an expression library, for example in λgt11 and screening the library with antibodies obtained from infected dogs or by labeling the proteins produced in these libraries.

As another alternative, antigens may be prepared from adult worms. Following humane euthanasia of dogs infected with *Dirofilaria immitis* the heart and lungs are removed, dissected and antigens are prepared from them. Adult female and male *D. immitis* are collected and separated by gender. Adult, exclusively male, *D. immitis* antigens are preferred for immunization.

The antigens, once isolated and characterized, may also be produced synthetically. A single antigen may be employed, or a crude or defined mixture of antigens may be utilized. The antigens are often proteins, but alternative antigens include other biomolecules derived from nematodes such as carbohydrates, lipids, and the like.

The vaccines of the invention are administered in a manner consistent with the nature of the vaccine; protein antigens are administered with conventional excipients for injection or other systemic administration. In addition to injection, transmucosal or transdermal delivery into the bloodstream may also be used using standard formulations for this purpose such as those described in *Remington's Pharmaceutical Sciences*, latest edition, Mack Publishing Company, Easton, Pa. The mode of administration, if properly formulated, may also be oral; however, systemic injection using standard adjuvants and excipients is preferred. Of course, the active ingredient may be a single antigen or a mixture of two or more.

Similarly, immunostimulants can be formulated in ways generally understood in the art and suitable for the immunostimulant of choice. Administration protocols are optimized for the specified host and the active ingredient.

The following examples are intended to illustrate but not to limit the invention.

EXAMPLE 1

Immunization of Cats with L4 Antigens

A. A general vaccine was prepared using D. immitis L4 larvae which have been cultured as described above. Frozen, thawed L4 s were homogenized in phosphate buffered saline with 0.1% Triton X-100. The homogenate contained about 1,000 L4/0.05 ml.

24 cats, 16 female and 8 male, were divided into a control group and an experimental group. The control group received 0.05 ml on day 0 in each hindlimb of equal volumes of Titermax (CytRx Corporation, Norcross, Ga.) adjuvant and PBS; the immune group received similar amounts of Titermax and homogenate. On day 28, the animals were boosted with injections as on day 0, except those animals immunized with larvae received half the dose of L4 (500 L4/0.05 ml).

On day 35, the animals were challenged with 100 L3 larvae per cat by subcutaneous inoculation in the inguinal region. On day 181, 4 immune and 4 control animals were necropsied, but showed little sign of infection. On day 205, 8 controls and 7 immunized animals were necropsied (one had died previously) and assessed for heartworm infection. The results showed that 5 of the 12 control cats were infected with at least one parasite; however, none of the immunized cats were infected.

B. In a second trial, 36 cats were divided into three groups, 12 cats per group, and each cat received 0.1 ml intramuscularly of either (1) a mixture of Titermax with extract prepared from 1,000 *D. immitis* L4 which had been homogenized as described in paragraph A in PBS/0.1% Triton X-100; (2) a second group received Titermax mixed with PBS/0.1% Triton X-100; and the (3) third group received only PBS/0.1% Triton X-100 on day 0. On day 28, each cat in group 1 received 0.1 ml Titermax plus the extract of 500 L4 *D. immitis* prepared as above; the second group received 0.5–0.75 ml of Titermax and PBS/0.1% Triton X-100; the third group received no injections. On day 43 the cats were challenged with 100 *D. immitis* L3 larvae and examined 24 weeks after the challenge.

EXAMPLE 2

Immunization of Cats with Male Adult Antigens

To prepare the vaccine, worms collected as described above are thoroughly washed in phosphate-buffered saline, drained, snap-frozen in liquid nitrogen and ground to a fine powder. This powder is resuspended in phosphate-buffered saline and sonicated. To determine dose, an aliquot is lyophilized and weighed. A total of 200 micrograms is administered twice, at Day 0 and Day 28. In a scaled-up procedure any method to produce a fine suspension of adult worm homogenate may be used.

Experimental animals (cats) are divided into control and test groups and administered antigen and adjuvant, adjuvant with PBS, or antigen alone. The adjuvant used in this protocol is Titermax.

Groups include:

|  | Group 1 | Group 2 | Group 3 | Group 4 | Group 5 |
| --- | --- | --- | --- | --- | --- |
| n | 9 | 9 | 10 | 10 | 10 |
| Day 0 | Antigen + adjuvant | Adjuvant | Antigen | Antigen + adjuvant | Adjuvant |
| Day 28 | Repeat Day 0 . . . |  |  |  |  |
| Day 112 | Challenge | Challenge | — | — | — |
| Day 196 | — | — | Challenge | Challenge | Challenge |

Necropsy to assess worm burdens is performed at 6 months after challenge.

EXAMPLE 3

Immunization of Cats with

Antigens from Free-Living Nematodes *C. elegans* are grown in bulk by standard procedures (The Nematode Caenorhabditis elegans, Cold Spring Harbor Laboratory, William B. Wood, ed., 1988), thoroughly washed and sonicated in M-9 buffer. To determine dose, an aliquot is lyophilized and weighed. A total of 200 micrograms is administered twice, at Day 0 and Day 28.

Experimental animals (cats) are divided into control and test groups and administered antigen and adjuvant, adjuvant and M-9 buffer or antigen alone. The adjuvant used is Titermax.

Groups of 10 cats each include:

| Day | Group 1 | Group 2 | Group 3 | Group 4 | Group 5 |
|---|---|---|---|---|---|
| 0 | Antigen + adjuvant | Adjuvant | Antigen | Antigen + adjuvant | Adjuvant |
| 28 | Repeat Day 0 . . . | | | | |
| 112 | Challenge | Challenge | — | — | — |
| 196 | — | — | Challenge | Challenge | Challenge |

Necropsy to assess worm burdens is performed at 6 months after challenge.

EXAMPLE 4

Effectiveness of Sindbis Constructs

The Sindbis constructs were prepared as follows:

Subcloning of RA cDNA

Di22 DNA (referenced hereinabove) contains a 399 base pair repeat which encodes a 15 Kd peptide designated RA. The DNA region corresponding to RA was amplified from Di22 DNA by polymerase chain reaction (PCR) using two synthetic oligonucleotides, P12 and P14, as described by Sambrook, J., et al., Molecular Cloning (1989).

P12: SEQ ID NO: 1

5' GTC GAC CCC GGG TCTAGA (XbaI) ACCATGG CTC TCA GTG AAA TCA 3'

P14: SEQ ID NO: 2

5' ACG CGT GGT AC CTCGAG (XhoI) TCA TCT GCA GCC TTC TTG AA 3'

These two oligonucleotides represent sequences complementary to the opposite strands of RA-encoding DNA at the 5' end of each strand flanked with restriction sites XbaI and XhoI. After double digestion with XbaI and XhoI, respectively, and gel purification, RA-encoding DNA was subcloned into Bluescript II sk (+) (Stratagene) designated BHA. This subclone was confirmed by restriction enzyme mapping.

Cloning RA Sequence Into Sindbis Vector

The XbaI to XhoI fragment which contains RA-encoding sequence of the plasmid BHA DNA was gel-purified. The purified RA-encoding DNA was ligated into the Sindbis expression vector Toto 2J1 designated HJA, so that when the Sindbis vector is expressed in baby hamster kidney (BHK) cells or infects a host, it produces the RA polypeptide encoded by the insert, as described by Xiong, C., et al., Science (1989) 243:188–1191 (See also, Huang et al. U.S. Ser. No. 07/296,454, incorporated herein by reference).

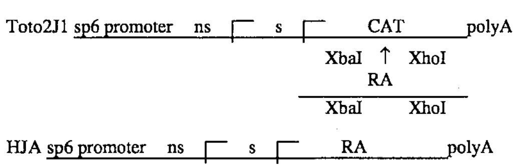

Cats were divided into five groups, and each cat received 1 ml subcutaneously into the nape of the neck:

Group 1 received $5\times10^7$ pfu HJA Sindbis construct (8 cats);

Group 2 is a duplicate of Group 1;

Group 3 received $5\times10^7$ pfu wild-type Sindbis (9 cats);

Group 4 received HBSS plus 1% FCS diluent (8 cats); and

Group 5 received $5\times10^7$ pfu first-passage HJA Sindbis construct (2 cats).

As a secondary immunization on day 28, the protocol for Group 1 was repeated; Group 2 received 0.1 ml Titermax plus 80 μg GST-22 fusion protein[1] intramuscularly; Group 3 received 0.1 ml Titermax and HBSS plus 1% FCS; Groups 4 and 5 repeated their previous protocols. The cats were challenged 56 days after day 0 with 100 *D. immitis* L3 subcutaneously. Examination for infection was conducted 24 weeks after challenge. [1] GST-22 fusion protein refers to a protein recombinantly produced in *E. coli* by expression of the insert into the expression vector pGEX-3X of a 1300-nucleotide fragment encoding the protein shown in FIG. 1. This fragment was recovered as described in detail in U.S. Ser. No. 07/683,202, filed 8 Apr. 1991 and incorporated herein by reference.

Sera were collected preimmunization, 1 month postprimary and secondary immunizations, and monthly postchallenge. On days 169 and 170 postchallenge, all cats were euthanized, necropsied, and inspected for the presence of adult *D. immitis*. The necropsy results were as follows: 0% of the cats in Groups 1, 3 and 5 had worms, 12.5% (1 cat out of 8 cats) in Group 2 had a single worm, and 50% (4 cats out of 8 cats) in Group 4 had one to three worms.

In accordance with these results, it can be concluded that use of Sindbis alone (Group 3) as well as the Sindbis construct containing the *D. immitis* -derived antigen is effective in protecting the subject host.

We claim:

1. A method to protect a feline host against infection by *D. immitis*, which method comprises stimulating the immune system of the host to elevated levels to inhibit the development of *D. immitis* worms in said host, said step of stimulating comprising administering to said host a protective amount of a homogenate of L4.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1:

GTCGACCCCG GGTCTAGAAC CATGGCTCTC AGTGAAATCA                                          40

( 2 ) INFORMATION FOR SEQ ID NO:2:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

ACGCGTGGTA CCTCGAGTCA TCTGCAGCCT TCTTGAA                                             37

( 2 ) INFORMATION FOR SEQ ID NO:3:

( i ) SEQUENCE CHARACTERISTICS:
      ( A ) LENGTH: 1284 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 1..1284

( x i ) SEQUENCE DESCRIPTION: SEQ ID NO:3:

| CGG | AAT | GAT | CAT | AAT | TTA | GAA | AGC | TAT | TTT | CAG | ACG | TAT | CTG | AGC | TGG | 48 |
| Arg | Asn | Asp | His | Asn | Leu | Glu | Ser | Tyr | Phe | Gln | Thr | Tyr | Leu | Ser | Trp | |
| 1 | | | | 5 | | | | | 10 | | | | | 15 | | |

| CTC | ACA | GAT | GCT | CAA | AAA | GAT | GAA | ATT | AAA | AAA | ATG | AAA | GAA | GAA | GGA | 96 |
| Leu | Thr | Asp | Ala | Gln | Lys | Asp | Glu | Ile | Lys | Lys | Met | Lys | Glu | Glu | Gly | |
| | | | 20 | | | | | 25 | | | | | 30 | | | |

| AAA | TCG | AAA | ATG | GAT | ATT | CAA | AAA | AAA | ATT | TTT | GAT | TAT | TTC | GAA | AGT | 144 |
| Lys | Ser | Lys | Met | Asp | Ile | Gln | Lys | Lys | Ile | Phe | Asp | Tyr | Phe | Glu | Ser | |
| | | 35 | | | | | 40 | | | | | 45 | | | | |

| TTG | ACA | GGT | GAT | AAA | AAG | AAA | AAG | GCT | GCA | GAA | GAA | CTT | CAA | CAA | GGT | 192 |
| Leu | Thr | Gly | Asp | Lys | Lys | Lys | Lys | Ala | Ala | Glu | Glu | Leu | Gln | Gln | Gly | |
| | 50 | | | | | 55 | | | | | 60 | | | | | |

| TGC | TTA | ATG | GCT | CTC | AGT | GAA | ATC | ATT | GGT | AAT | GAA | AAG | ATG | CTT | ATG | 240 |
| Cys | Leu | Met | Ala | Leu | Ser | Glu | Ile | Ile | Gly | Asn | Glu | Lys | Met | Leu | Met | |
| 65 | | | | | 70 | | | | | 75 | | | | | 80 | |

| TTG | AAA | GAG | ATT | AAA | GAT | TCA | GGC | GCT | GAT | CCA | GAA | CAA | ATC | AGA | ATG | 288 |
| Leu | Lys | Glu | Ile | Lys | Asp | Ser | Gly | Ala | Asp | Pro | Glu | Gln | Ile | Arg | Met | |
| | | | | 85 | | | | | 90 | | | | | 95 | | |

| AAA | GTC | GAA | GAT | ATG | TTG | AAA | CTT | GTC | GTT | GAC | AAA | GAA | AAG | AAG | AAA | 336 |
| Lys | Val | Glu | Asp | Met | Leu | Lys | Leu | Val | Val | Asp | Lys | Glu | Lys | Lys | Lys | |
| | | | 100 | | | | | 105 | | | | | 110 | | | |

| AGA | ATT | GAT | GAA | TAT | GCT | CCT | GTA | TGC | CGT | AAA | ATT | TAT | GCG | GCA | ATG | 384 |
| Arg | Ile | Asp | Glu | Tyr | Ala | Pro | Val | Cys | Arg | Lys | Ile | Tyr | Ala | Ala | Met | |

-continued

|     | 115 |     |     |     | 120 |     |     |     | 125 |     |     |     |     |
|-----|-----|-----|-----|-----|-----|-----|-----|-----|-----|-----|-----|-----|-----|
| AAT | GAA | CGG | CGT | AAG | CGG | AAT | GAT | CAT | AAT | TTA | GAA | AGC | TAT | TTT | CAG | 432 |
| Asn | Glu | Arg | Arg | Lys | Arg | Asn | Asp | His | Asn | Leu | Glu | Ser | Tyr | Phe | Gln |
|     | 130 |     |     |     | 135 |     |     |     |     | 140 |     |     |     |     |     |

```
ACG TAT CTG AGC TGG CTC ACA GAT GCT CAA AAA GAT GAA ATT AAA AAA   480
Thr Tyr Leu Ser Trp Leu Thr Asp Ala Gln Lys Asp Glu Ile Lys Lys
145             150             155             160

ATG AAA GAA GAA GGA AAA TCG AAA ATG GAT ATT CAA AAA AAA ATT TTT   528
Met Lys Glu Glu Gly Lys Ser Lys Met Asp Ile Gln Lys Lys Ile Phe
            165             170             175

GAT TAT TTC GAA AGT TTG ACA GGT GAT AAA AAG AAA AAG GCT GCA GAA   576
Asp Tyr Phe Glu Ser Leu Thr Gly Asp Lys Lys Lys Lys Ala Ala Glu
        180             185             190

GAA CTT CAA GAA GGC TGC AGA ATG GCT CTG AGA GAA ATT GTT GGT GAA   624
Glu Leu Gln Glu Gly Cys Arg Met Ala Leu Arg Glu Ile Val Gly Glu
    195             200             205

GAG AAG TGG ACT GTA TTG AGG CAA ATG AAG GAT TCA GGC GCA ACT CCA   672
Glu Lys Trp Thr Val Leu Arg Gln Met Lys Asp Ser Gly Ala Thr Pro
210             215             220

AAG GAA CTA AGC ATG AAA GTT GAA GAG ATG TTC AAA GAT GTC GTT GAC   720
Lys Glu Leu Ser Met Lys Val Glu Glu Met Phe Lys Asp Val Val Asp
225             230             235             240

AAA GAT AAA AAG GAA AAA ATT GAT GAA TAT GCT CCT GTA TGC CGT AAA   768
Lys Asp Lys Lys Glu Lys Ile Asp Glu Tyr Ala Pro Val Cys Arg Lys
            245             250             255

ATC TTT GCG GTG ATA CAT GAA AGG CGT AAG CGG AAT GAT CAT AAT TTA   816
Ile Phe Ala Val Ile His Glu Arg Arg Lys Arg Asn Asp His Asn Leu
        260             265             270

GAA AGC TAT TTT CAA ACG TAT CTG AGC TGG CTC ACA GAT GCT CAA AAA   864
Glu Ser Tyr Phe Gln Thr Tyr Leu Ser Trp Leu Thr Asp Ala Gln Lys
    275             280             285

GAT GAA ATT AAA AAA ATG AAA GAA GAA GGA AAA TCG AAA ATG GAT ATT   912
Asp Glu Ile Lys Lys Met Lys Glu Glu Gly Lys Ser Lys Met Asp Ile
290             295             300

CAA AAA AAA ATT TTT GAT TAT TTC GAA AGT TTG ACA GGT GAT AAA AAG   960
Gln Lys Lys Ile Phe Asp Tyr Phe Glu Ser Leu Thr Gly Asp Lys Lys
305             310             315             320

AAA AAG GCT GCA GAA GAA CTT CAA GAA GGC TGC AGA ATG GCT CTG AGA  1008
Lys Lys Ala Ala Glu Glu Leu Gln Glu Gly Cys Arg Met Ala Leu Arg
            325             330             335

GAA ATT GTT GGT GAA GAG AAG TGG ACT GTA TTG AGG CAA ATG AAG GAT  1056
Glu Ile Val Gly Glu Glu Lys Trp Thr Val Leu Arg Gln Met Lys Asp
        340             345             350

TCA GGC GCA ACT CCA AAG GAA CTA AGC ATG AAA GTT GAA GAG ATG TTC  1104
Ser Gly Ala Thr Pro Lys Glu Leu Ser Met Lys Val Glu Glu Met Phe
    355             360             365

AAA GAT GTC GTT GAC AAA GAT AAA AAG GAA AAA ATT GAT GAA TAT GCT  1152
Lys Asp Val Val Asp Lys Asp Lys Lys Glu Lys Ile Asp Glu Tyr Ala
370             375             380

CCT GTA TGC CGT AAA ATC TTT GCG GTG ATA CAT GAA AGG CGT AAG CGG  1200
Pro Val Cys Arg Lys Ile Phe Ala Val Ile His Glu Arg Arg Lys Arg
385             390             395             400

AAT GAT CAT AAT TTA GAA AGC TAT TTT CAA ACG TAT CTG AGC TGG CTC  1248
Asn Asp His Asn Leu Glu Ser Tyr Phe Gln Thr Tyr Leu Ser Trp Leu
            405             410             415

ACG GAT GCT CAA AAA GAT GAA ATT AAA AAA AAA AAA                  1284
Thr Asp Ala Gln Lys Asp Glu Ile Lys Lys Lys Lys
        420             425
```

( 2 ) INFORMATION FOR SEQ ID NO:4:

( i ) SEQUENCE CHARACTERISTICS:
    ( A ) LENGTH: 428 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Arg  Asn  Asp  His  Asn  Leu  Glu  Ser  Tyr  Phe  Gln  Thr  Tyr  Leu  Ser  Trp
 1                    5                        10                         15

Leu  Thr  Asp  Ala  Gln  Lys  Asp  Glu  Ile  Lys  Lys  Met  Lys  Glu  Glu  Gly
              20                        25                   30

Lys  Ser  Lys  Met  Asp  Ile  Gln  Lys  Lys  Ile  Phe  Asp  Tyr  Phe  Glu  Ser
         35                        40                        45

Leu  Thr  Gly  Asp  Lys  Lys  Lys  Ala  Ala  Glu  Glu  Leu  Gln  Gln  Gly
     50                        55                        60

Cys  Leu  Met  Ala  Leu  Ser  Glu  Ile  Ile  Gly  Asn  Glu  Lys  Met  Leu  Met
65                        70                        75                         80

Leu  Lys  Glu  Ile  Lys  Asp  Ser  Gly  Ala  Asp  Pro  Glu  Gln  Ile  Arg  Met
                   85                        90                        95

Lys  Val  Glu  Asp  Met  Leu  Lys  Leu  Val  Val  Asp  Lys  Glu  Lys  Lys  Lys
              100                       105                      110

Arg  Ile  Asp  Glu  Tyr  Ala  Pro  Val  Cys  Arg  Lys  Ile  Tyr  Ala  Ala  Met
              115                       120                      125

Asn  Glu  Arg  Arg  Lys  Arg  Asn  Asp  His  Asn  Leu  Glu  Ser  Tyr  Phe  Gln
     130                       135                      140

Thr  Tyr  Leu  Ser  Trp  Leu  Thr  Asp  Ala  Gln  Lys  Asp  Glu  Ile  Lys  Lys
145                       150                      155                     160

Met  Lys  Glu  Glu  Gly  Lys  Ser  Lys  Met  Asp  Ile  Gln  Lys  Lys  Ile  Phe
                   165                       170                     175

Asp  Tyr  Phe  Glu  Ser  Leu  Thr  Gly  Asp  Lys  Lys  Lys  Ala  Ala  Glu
              180                       185                      190

Glu  Leu  Gln  Glu  Gly  Cys  Arg  Met  Ala  Leu  Arg  Glu  Ile  Val  Gly  Glu
          195                       200                       205

Glu  Lys  Trp  Thr  Val  Leu  Arg  Gln  Met  Lys  Asp  Ser  Gly  Ala  Thr  Pro
     210                       215                      220

Lys  Glu  Leu  Ser  Met  Lys  Val  Glu  Glu  Met  Phe  Lys  Asp  Val  Val  Asp
225                       230                       235                    240

Lys  Asp  Lys  Lys  Glu  Lys  Ile  Asp  Glu  Tyr  Ala  Pro  Val  Cys  Arg  Lys
                   245                       250                     255

Ile  Phe  Ala  Val  Ile  His  Glu  Arg  Arg  Lys  Arg  Asn  Asp  His  Asn  Leu
              260                       265                      270

Glu  Ser  Tyr  Phe  Gln  Thr  Tyr  Leu  Ser  Trp  Leu  Thr  Asp  Ala  Gln  Lys
          275                       280                       285

Asp  Glu  Ile  Lys  Lys  Met  Lys  Glu  Glu  Gly  Lys  Ser  Lys  Met  Asp  Ile
     290                       295                      300

Gln  Lys  Lys  Ile  Phe  Asp  Tyr  Phe  Glu  Ser  Leu  Thr  Gly  Asp  Lys  Lys
305                       310                       315                    320

Lys  Lys  Ala  Ala  Glu  Glu  Leu  Gln  Glu  Gly  Cys  Arg  Met  Ala  Leu  Arg
              325                       330                      335

Glu  Ile  Val  Gly  Glu  Glu  Lys  Trp  Thr  Val  Leu  Arg  Gln  Met  Lys  Asp
              340                       345                      350

Ser  Gly  Ala  Thr  Pro  Lys  Glu  Leu  Ser  Met  Lys  Val  Glu  Glu  Met  Phe
          355                       360                       365

Lys  Asp  Val  Val  Asp  Lys  Asp  Lys  Lys  Glu  Lys  Ile  Asp  Glu  Tyr  Ala
```

|   |   |   |   |   | 370 |   |   |   |   | 375 |   |   |   |   | 380 |   |   |   |   |
|---|---|---|---|---|---|---|---|---|---|---|---|---|---|---|---|---|---|---|---|

Pro Val Cys Arg Lys Ile Phe Ala Val Ile His Glu Arg Arg Lys Arg
385                 390             395                 400

Asn Asp His Asn Leu Glu Ser Tyr Phe Gln Thr Tyr Leu Ser Trp Leu
                405             410              415

Thr Asp Ala Gln Lys Asp Glu Ile Lys Lys Lys Lys
             420             425